(12) United States Patent
Reisacher et al.

(10) Patent No.: US 10,456,534 B2
(45) Date of Patent: Oct. 29, 2019

(54) NASAL SPRAY DELIVERY GUIDE

(71) Applicants: Cornell University, Ithaca, NY (US); Nasalign LLC, New York, NY (US)

(72) Inventors: William Reisacher, New York, NY (US); Erick B. Berglund, New York, NY (US); Michael Nelson, New York, NY (US)

(73) Assignees: Cornell University, Ithica, NY (US); Nasalign LLC, New York, NY (US)

( * ) Notice: Subject to any disclaimer, the term of this patent is extended or adjusted under 35 U.S.C. 154(b) by 923 days.

(21) Appl. No.: 14/974,124

(22) Filed: Dec. 18, 2015

(65) Prior Publication Data

US 2016/0101243 A1    Apr. 14, 2016

Related U.S. Application Data

(63) Continuation of application No. PCT/US2014/042973, filed on Jun. 18, 2014.
(Continued)

(51) Int. Cl.
*A61M 11/00* (2006.01)
*A61M 15/08* (2006.01)
(Continued)

(52) U.S. Cl.
CPC .............. *A61M 11/00* (2013.01); *A61F 5/08* (2013.01); *A61M 15/085* (2014.02); *A61M 11/08* (2013.01); *A61M 2209/088* (2013.01)

(58) Field of Classification Search
CPC .... A61M 11/00; A61M 11/08; A61M 15/085; A61M 15/08; A61B 17/24;
(Continued)

(56) References Cited

U.S. PATENT DOCUMENTS 1,256,188 A   2/1918  Wilson
1,903,410 A   1/1933  Cecil
(Continued)

OTHER PUBLICATIONS

Mathiowetz et al, Grip and Pinch Strength: Normative Data for Adults, 1985, Arch Phys Med Rehabil., 66, 69-74.*
(Continued)

*Primary Examiner* — Tan-Uyen T Ho
*Assistant Examiner* — Margaret M Luarca
(74) *Attorney, Agent, or Firm* — Eversheds Sutherland (US) LLP (57) ABSTRACT

A nasal spray delivery guide including a pair of guide elements spaced apart from one another and configured to be at least partially inserted into respective nostrils of a patient, and a flexible connector element attached to and extending between the guide elements. Each guide element includes an aperture extending therethrough from a base end to a tip end of the guide element. A method for delivering a nasal spray into a patient's nose includes the steps of providing the nasal spray delivery guide, inserting the guide elements at least partially into respective nostrils of the patient, inserting at least a portion of a nasal spray delivery device into one of the guide elements, and activating the nasal spray delivery device to deliver a nasal spray to a lateral wall of the respective nasal cavity.

21 Claims, 7 Drawing Sheets

Related U.S. Application Data (60) Provisional application No. 61/836,207, filed on Jun. 18, 2013.

(51) Int. Cl.
*A61F 5/08* (2006.01)
*A61M 11/08* (2006.01)

(58) Field of Classification Search
CPC .......... A61B 17/3423; A61B 17/12104; A61B 1/00054; A61F 5/08
USPC ...... 606/199, 204.45, 108; 128/200, 200.14; 604/94.01
See application file for complete search history.

(56) References Cited

U.S. PATENT DOCUMENTS

| | | |
|---|---|---|
| 2,569,743 A | 10/1951 | Carlock |
| 2,672,138 A | 3/1954 | Carlock |
| 5,544,783 A | 8/1996 | Conigliaro |
| 6,145,703 A | 11/2000 | Opperman |
| 2002/0177871 A1 | 11/2002 | Santin |
| 2006/0085027 A1 | 4/2006 | Santin |
| 2006/0169285 A1 | 8/2006 | Bovo |
| 2013/0092173 A1 | 4/2013 | Alexander et al. |

OTHER PUBLICATIONS

PCT International Search Report and Written Opinion for PCT Application No. PCT/US2014/042973 dated Dec. 17, 2014 (11 pages).

European Search Report for EP Application No. 148129166.6 dated Jan. 16, 2017 (7 pages).

\* cited by examiner

NASAL SPRAY DELIVERY GUIDE

CROSS-REFERENCE TO RELATED APPLICATION

This application is a continuation of PCT Application No. PCT/US2014/042973, filed Jun. 18, 2014, which claims the benefit of U.S. Provisional Application No. 61/836,207, filed Jun. 18, 2013, the entire contents of which are incorporated herein by reference.

FIELD OF THE DISCLOSURE

The present disclosure relates generally to devices, systems, and methods for delivery of a nasal spray, and more particularly to nasal spray delivery guides, nasal spray delivery systems, and related methods for facilitating delivery of a nasal spray.

BACKGROUND OF THE DISCLOSURE

Nasal sprays are common drug-delivery vehicles for a wide variety of medications, both OTC and prescription. The permeable and highly vascularized mucosa provides a large surface area for absorption of both local and systemic medications, with rapid onset of therapeutic action and avoidance of "first pass" metabolism through the liver. Examples of commonly used nasal sprays include nasal saline, AFRIN, ZICAM, intranasal steroids, intranasal antihistamines, ZOMIG, and the flu vaccine.

Various spray devices are used for delivering nasal sprays. In addition to the characteristics of the spray device itself, it has been determined that the handling of the device during application plays a significant role in the optimization of the drug delivery. Specific factors include positioning of the head, determining the correct angle to hold the spray device and determining how far to insert the device into the nostrils. Although there is general consensus concerning these factors, the vast majority of patients are either not instructed on how to use the spray device or fail to follow the given instructions accurately. Because patients cannot see the spray device entering the nose, unless viewed in a mirror, orienting the hand properly becomes extremely difficult, particularly for those patients with arthritis or other physical limitations.

Improper delivery of a nasal spray may lead to several unwanted outcomes. If the spray does not reach the intended target in the nose, it will not be as effective for the patient and will likely not be continued. This will happen, for example, if the spray is directed to the back of the throat or medially towards the nasal septum. Moreover, if the spray is swallowed, it may cause sore throat and a bad taste in the mouth. Epistaxis often occurs if the spray is directed towards the nasal septum, and septal ulcerations and perforations have been reported from direction of intranasal steroids to this region. The ideal application of nasal spray is at an angle of approximately 30 degrees from the floor of the nose, directed towards the lateral nasal wall.

Thus, there is a need for improved devices, systems, and methods for delivery of a nasal spray. Such devices and systems should provide ease of use and facilitate proper delivery of the nasal spray in order to avoid the foregoing unwanted outcomes.

SUMMARY OF THE DISCLOSURE

In one aspect, the present disclosure provides a nasal spray delivery guide including a pair of guide elements spaced apart from one another and configured to be at least partially inserted into respective nostrils of a patient, and a flexible connector element attached to and extending between the guide elements. Each guide element includes an aperture extending therethrough from a base end to a tip end of the guide element.

In another aspect, the present disclosure provides a method for delivering a nasal spray into a patient's nose. The method includes the step of providing a nasal spray delivery guide comprising a pair of guide elements spaced apart from one another, and a flexible connector element attached to and extending between the guide elements. Each guide element includes an aperture extending therethrough from a base end to a tip end of the guide element. The method also includes the steps of inserting the guide elements at least partially into respective nostrils of the patient, inserting at least a portion of a nasal spray delivery device into one of the guide elements, and activating the nasal spray delivery device to deliver a nasal spray to a lateral wall of the respective nasal cavity.

In still another aspect, the present disclosure provides a nasal spray delivery system including a nasal spray delivery device, a nasal spray delivery guide, and a clip removably attached to the nasal spray delivery device, wherein the nasal spray delivery guide is removably coupled to the nasal spray delivery device via the clip. The nasal spray delivery guide includes a pair of guide elements spaced apart from one another and configured to be at least partially inserted into respective nostrils of a patient, and a flexible connector element attached to and extending between the guide elements. Each guide element includes an aperture extending therethrough from a base end to a tip end of the guide element.

These and other aspects and embodiments of the present disclosure will become apparent to one of ordinary skill in the art upon review of the following detailed description when taken in conjunction with the several drawings and the appended claims.

BRIEF DESCRIPTION OF THE DRAWINGS

The detailed description is set forth with reference to the accompanying drawings, which are not necessarily drawn to scale. Use of the same reference numerals indicates similar or identical items. Certain embodiments of the present disclosure may utilize elements, components, and/or configurations other than those illustrated in the drawings, and some elements, components, and/or configurations may not be present in certain embodiments.

DETAILED DESCRIPTION OF THE DISCLOSURE

In the following description, reference is made to the accompanying drawings that form a part hereof, and in which is shown by way of illustration specific example embodiments which may be practiced. These example embodiments are described in detail to enable those skilled in the art to practice the devices, systems, and methods of the present disclosure, and it is to be understood that other embodiments may be utilized and that logical changes may be made without departing from the scope of the present disclosure. The following description of example embodiments is, therefore, not to be taken in a limited sense, as the scope of the present invention is defined by the appended claims.

The Abstract is provided to comply with 37 C.F.R. § 1.72(b) to allow the reader to quickly ascertain the nature and gist of the present disclosure. The Abstract is submitted with the understanding that it will not be used to interpret or limit the scope or meaning of the claims.

In one aspect, the present disclosure provides a nasal spray delivery guide for facilitating delivery of a nasal spray easily and accurately into a patient's nose, directing the spray to a lateral wall of a nasal cavity, and avoiding the septum and the back of the nose. The nasal spray delivery guide also prevents over-insertion of a nasal spray delivery device, thereby preventing injury of the inside of the nose.

Figure 1A:
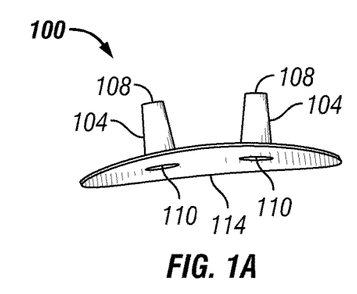
FIG. 1A shows a bottom perspective view of a nasal spray delivery guide according to one example embodiment of the present disclosure, the nasal spray delivery guide in a stable, convex conformation.
Figure 1B:
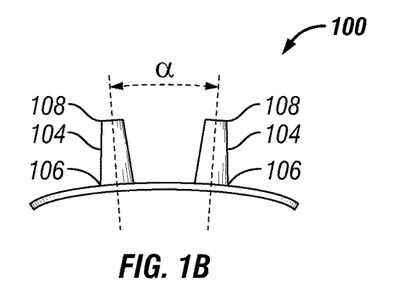
FIG. 1B shows a front view of the nasal spray delivery guide of FIG. 1A in the stable, convex conformation.
Figure 1C:
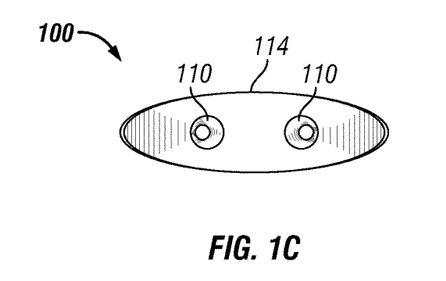
FIG. 1C shows a bottom view of the nasal spray delivery guide of FIG. 1A in the stable, convex conformation.
Figure 1D:
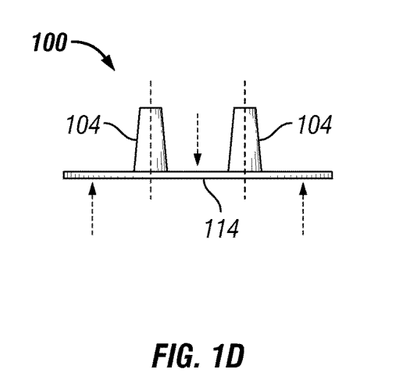
FIG. 1D shows a front view of the nasal spray delivery guide of FIG. 1A in a non-stable, flattened conformation, with arrows generally showing the direction of pressure applied to achieve the non-stable, flattened conformation.
Figure 1E:
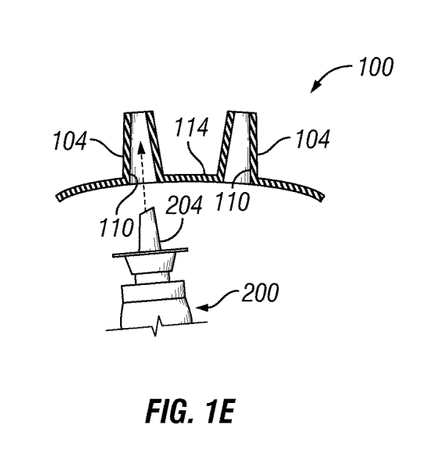
FIG. 1E shows a front cross-sectional view of the nasal spray delivery guide of FIG. 1A in the stable, convex conformation and a nasal spray delivery device approaching a guide element of the nasal spray delivery guide.

FIGS. 1A-1E show a nasal spray delivery guide 100 (also referred to herein simply as a "delivery guide") for facilitating delivery of a nasal spray into a patient's nose, according to one example embodiment of the present disclosure. The delivery guide 100 may include at least one guide element 104 configured to be inserted at least partially into a nostril of the patient and to receive at least a portion of a nasal spray delivery device 200 therein. As is shown, the guide element 104 may have an elongated shape including a base end 106 and a tip end 108. The guide element 104 may be hollow in nature, including an aperture 110 extending longitudinally therethrough from the base end 106 to the tip end 108. In this manner, a portion of the nasal spray delivery device 200, such as a nozzle 204 thereof, may be inserted into the aperture 110 during use, as is shown in FIG. 1E. In some embodiments, the guide element 104 may be filled with a compressible substance, such as a foam or a gel, configured to allow penetration by the nozzle 204 of the nasal spray delivery device 200.

The guide element 104 may have any shape suitable for safely inserting into the nostril of the patient and for receiving a portion of the spray delivery device 200. As is shown, the guide element 104 may have a generally conical shape with axial cross-sections of the guide element 104 decreasing from the base end 106 to the tip end 108. In such embodiments, the axial cross-sections may have a generally circular, oval, or oblong shape of varying dimensions. Alternatively, the guide element 104 may have a generally tubular shape with axial cross-sections of the guide element 104 of the same dimensions from the base end 106 to the tip end 108. In such embodiments, the axial cross-sections may have a generally circular, oval, or oblong shape. As another alternative, the guide element 104 may have a generally prismatic shape with axial cross-sections of the guide element 104 decreasing from the base end 106 to the tip end 108. In such embodiments, the axial cross-sections may have a generally square, rectangular, trapezoidal, or other polygonal shape of varying dimensions.

The guide element 104 may be sized to fit comfortably into the nasal vestibule of the patient. Due to variation in the sizes of human noses, the delivery guide 100 may be manufactured in different sizes such that, for example, the guide element 104 is suitable for insertion into a child's nose or an adult's nose. In some embodiments in which the guide element 104 has a generally conical shape, at the base end 106, the aperture 110 may have a diameter between approximately 1 cm and approximately 3 cm, or between approximately 1.5 cm and approximately 2.5 cm, or of approximately 2 cm. In some embodiments, at the tip end 108 of the guide element 104, the aperture 110 may have a diameter between approximately 0.3 cm and approximately 2 cm, or between approximately 0.5 cm and approximately 1.5 cm, or of approximately 1 cm. In some embodiments, the guide element 104 may have a height, measured from the base end 106 to the tip end 108, between approximately 0.3 cm and approximately 2 cm, or between approximately 0.5 cm and approximately 1.5 cm, or of approximately 1 cm. In some embodiments, the guide element 104 may have a wall thickness between approximately 0.5 mm and approximately 10.0 mm, or between approximately 1.0 mm and approximately 7.0 mm, or of approximately 3 mm. The wall thickness may be generally constant from the base end 106 to the tip end 108 of the guide element 104. Alternatively, the wall thickness may vary from the base end 106 to the tip end 108 of the guide element 104. For example, the wall thickness may be greater at the base end 106 than the tip end 108, or vice versa. For embodiments in which the guide element 104 has a non-conical shape, such as one of the other shapes described above, the aperture 110, the height, and the wall thickness of the guide element may be dimensioned in a similar manner.

The guide element 104 may be formed of a material suitable for safely inserting into the nostril of the patient and for receiving a portion of the spray delivery device 200. In some embodiments, the guide element 104 may be formed of a pliable polymer, such as an elastomeric polymer, having a durometer between approximately 10 and approximately 40 on the Shore A scale, or between approximately 15 and approximately 35 on the Shore A scale. Examples of such polymers include, but are not limited to, silastic, silicone, and PVC. In some embodiments, the polymer may include one or more coloring agents therein.

As is shown, the nasal spray delivery guide 100 may include a pair of guide elements 104 configured to be inserted at least partially into respective nostrils of the patient. The delivery guide 100 may have at least one stable conformation in which an angle α between the longitudinal axes of the guide elements 104 is fixed, as is shown in FIGS. 1A-1C. In some embodiments, the fixed angle α between the longitudinal axes of the guide elements 104 may be between approximately 10 degrees and approximately 30 degrees, or between approximately 15 degrees and approximately 25 degrees, or approximately 20 degrees. In this manner, upon insertion of the guide elements 104 into the patient's nostrils, each guide element 104 may be configured to direct a nasal spray to a lateral wall of the respective nostril, avoiding the septum and the back of the nose. Specifically, each guide element 104 may be configured to direct the nasal spray to the lateral wall at an angle from the septum that is equal to approximately one-half of the angle α between the longitudinal axes of the guide elements 104. Further, upon insertion of the guide elements 104 into the patient's nostrils, each guide element 104 may be configured to direct the nasal spray to the lateral wall at an angle from the floor of the patient's nose of between approximately 20 degrees and approximately 40 degrees, or between approximately 25 degrees and approximately 35 degrees, or approximately 30 degrees.

The delivery guide 100 may be flexible enough such that it may be temporarily deformed into a non-stable conformation under physical pressure typical of the human hand (for example, by application of a force of between approximately 0.5 Newtons and approximately 15 Newtons), although the delivery guide 100 will return to its stable conformation after such pressure is released. For example, the delivery guide 100 may be temporarily deformed into a non-stable, flattened conformation in which the longitudinal axes of the guide elements 104 are parallel to one another (i.e., the angle α between the longitudinal axes of the guide elements 104 is zero), as is shown in FIG. 1D. In some embodiments, the delivery guide 100 may have at least two stable conformations. For example, the delivery guide 100 may have a first stable conformation, as is shown in FIGS. 1A-1C, and a second stable conformation, as is shown in FIG. 1D. In this manner, the delivery guide 100 may be selectively movable between the first stable conformation and the second stable conformation.

As is shown, the pair of guide elements 104 may be spaced apart from one another. In some embodiments, a distance between the adjacent edges of the base ends 106 of the guide elements 104 may be between approximately 0 cm and approximately 1.5 cm, or between 0.5 cm and approximately 1 cm, or approximately 0.75 cm. Alternatively, the adjacent edges of the base ends 106 of the guide elements 104 may abut one another such that the guide elements 104 are not spaced apart from one another (i.e., there is no distance between the adjacent edges of the base ends 106 of the guide elements 104). In this manner, the base ends 106 of the guide elements 104 may form a joint. As another alternative, the base ends 106 of the guide elements 104 may overlap one another such that a negative distance exists between the base ends 106 (i.e., the guide elements 104 may share an edge at the base ends 106 via an indentation of both guide elements 104). In this manner, the base ends 106 of the guide elements 104 may form a joint. The negative distance between the base ends 106 may be between approximately −2 cm and approximately 0 cm, or between approximately −1.5 cm and approximately −0.5 cm, or approximately −1 cm.

In some embodiments in which the delivery guide 100 includes a pair of guide elements 104 abutting one another (i.e., having no distance therebetween) or overlapping one another (i.e., having a negative distance therebetween), the delivery guide 100 may have at least one stable conformation in which an angle α between the longitudinal axes of the guide elements 104 is fixed. The fixed angle α between the longitudinal axes of the guide elements 104 may be between approximately 10 degrees and approximately 30 degrees, or between approximately 15 degrees and approximately 25 degrees, or approximately 20 degrees. The joint between the guide elements 104 may be flexible enough such that the delivery guide 100 may be temporarily deformed into a non-stable conformation under physical pressure typical of the human hand (for example, by application of a force of between approximately 0.5 Newtons and approximately 15 Newtons), although the delivery guide 100 will return to its stable conformation after such pressure is released. For example, the delivery guide 100 may be temporarily deformed into a non-stable conformation in which the longitudinal axes of the guide elements 104 are parallel to one another (i.e., the angle α between the longitudinal axes of the guide elements 104 is zero).

In some embodiments in which the delivery guide 100 includes a pair of guide elements 104 spaced apart from one another, the delivery guide 100 may include a flexible connector element 114 attached to and extending between the guide elements 104, as is shown. The flexible connector element 114 may have at least one stable conformation in which an angle α between the longitudinal axes of the guide elements 104 is fixed, as is shown in FIGS. 1A-1C. In some embodiments, the fixed angle α between the longitudinal axes of the guide elements 104 may be between approximately 10 degrees and approximately 30 degrees, or between approximately 15 degrees and approximately 25 degrees, or approximately 20 degrees. The flexible connector element 114 may be flexible enough such that it may be temporarily deformed into a non-stable conformation under physical pressure typical of the human hand (for example, by application of a force of between approximately 0.5

Newtons and approximately 15 Newtons), although the flexible connector element 114 will return to its stable conformation after such pressure is released. For example, the flexible connector element 114 may be temporarily deformed into a non-stable flattened conformation in which the longitudinal axes of the guide elements 104 are parallel to one another (i.e., the angle α between the longitudinal axes of the guide elements 104 is zero), as is shown in FIG. 1D. In some embodiments, the flexible connector element 114 may have at least two stable conformations. For example, the flexible connector element 114 may have a first stable conformation, as is shown in FIGS. 1A-1C, and a second stable conformation, as is shown in FIG. 1D. In this manner, the flexible connector element 114 may be selectively movable between the first stable conformation and the second stable conformation.

In some embodiments, the flexible connector element 114 is formed of a pliable polymer, which may be a memory polymer such as a pseudoelastomer, or an elastomer, having a durometer between approximately 10 and approximately 40 on the Shore A scale, or between approximately 15 and approximately 35 on the Shore A scale. The flexible connector element 114 may be formed of the same polymer as the guide elements 104.

As is shown in FIGS. 1A-1E, the flexible connector element 114 may be in the form of a sheet. In some embodiments, the sheet may have a regular shape when viewed from the top or the bottom, such as a rectangle or an oval (as is shown in FIGS. 1A-1E). Alternatively, the sheet may have an irregular shape when viewed from the top or the bottom. For example, the sheet may include a curved cutout to accommodate the curvature of a human face, and/or the sheet may include curvatures to accommodate the philtrum and aid in properly positioning the delivery guide 100 relative to the patient's nose. In some embodiments, the sheet may include an additional lip around and/or between the guide elements 104. The dimensions of the sheet are sufficient to accommodate the guide elements 104. In some embodiments, the sheet may have an overall length (i.e., the longest distance from edge to edge of the sheet, measured on an axis that passes through the center of each guide element 104) of between approximately 2 cm and approximately 10 cm, or between approximately 4 cm and approximately 8 cm. In some embodiments, the sheet may have an overall width (i.e., the longest distance from edge to edge of the sheet, measured on an axis that is perpendicular to the axis that passes through the center of each guide element 104) of between approximately 1 cm and approximately 6 cm, or between approximately 2 cm and approximately 5 cm. In some embodiments, the sheet may have a thickness (i.e., the distance between the top surface and the bottom surface of the sheet) of between approximately 0.5 mm and approximately 10.0 mm, or between approximately 1.0 mm and approximately 7.0 mm, or of approximately 3 mm. The thickness of the sheet may be generally constant over the length and width of the sheet.

In some embodiments in which the delivery guide 100 includes the flexible connector element 114 in the form of a sheet, the delivery guide 100 may be manufactured by injection molding the sheet and the guide elements 104 in a stable, convex conformation in which the approximate center of the arc forming the curvature is located on the opposite side (the bottom side) of the sheet from the guide elements 104 (on the top side), as is shown in FIGS. 1A-1C. In this manner, the longitudinal axes of the guide elements 104 extend through the approximate center of the arc, and an angle α between the longitudinal axes of the guide elements 104 is fixed. In some embodiments, the fixed angle α between the longitudinal axes of the guide elements 104 may be between approximately 10 degrees and approximately 30 degrees, or between approximately 15 degrees and approximately 25 degrees, or approximately 20 degrees. The curvature of the sheet required to create a desired angle α will depend on the placement of the guide elements 104 relative to one another on the sheet, and such curvature can easily be determined by one skilled in the art. Alternatively, the sheet may be formed by injecting molding the sheet in a concave conformation, such that when pressure is applied to the bottom of the finished sheet, it can also take a convex conformation as described above.

Figure 2A:
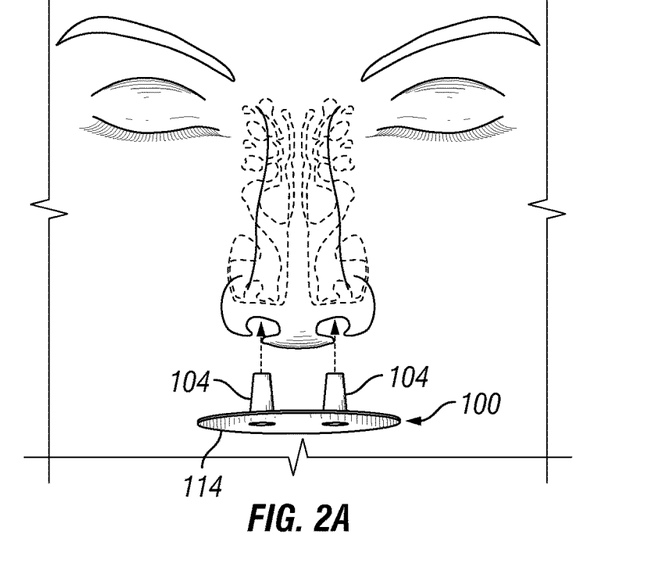
FIG. 2A shows a front view of the nasal spray delivery guide of FIG. 1A in the non-stable, flattened conformation and approaching a nose of a patient.
Figure 2B:
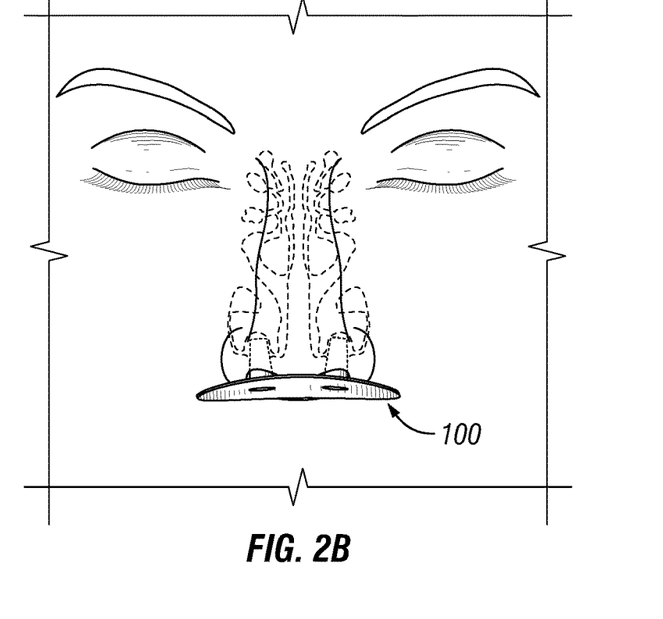
FIG. 2B shows a front view of the nasal spray delivery guide of FIG. 1A in the stable, convex conformation with guide elements of the nasal spray delivery guide inserted within the nostrils of the patient's nose to direct a nasal spray to lateral walls of the respective nasal cavities.

FIGS. 2A and 2B show the nasal spray delivery guide 100 being inserted into a patient's nose for use. Initially, the delivery guide 100 may be grasped, and a force may be applied thereto such that the delivery guide 100 is temporarily deformed into the non-stable conformation such that the guide elements 104 are oriented for ease of insertion into the respective nostrils. For example, the delivery guide 100 may be temporarily deformed into the non-stable, flattened conformation, as is shown in FIG. 2A. The guide elements 104 then may be at least partially inserted into the respective nostrils. Following insertion of the guide elements 104, the force applied to the delivery guide 100 may be released such that the delivery guide 100 returns to the stable conformation. For example, the delivery guide 100 may return to the stable, convex conformation, as is shown in FIG. 2B. The nozzle 204 of the nasal spray delivery device 200 then may be inserted into one of the guide elements 104, and the nasal spray delivery device 200 may be activated to deliver the nasal spray to the lateral wall of the respective nasal cavity, while avoiding the septum and the back of the nose. As described above, the guide element 104 may direct the nasal spray to the lateral wall at an angle from the septum that is equal to approximately one-half of the angle α between the longitudinal axes of the guide elements 104. Further, the guide element 104 may direct the nasal spray to the lateral wall at an angle of between approximately 20 degrees and approximately 40 degrees from the floor of the patient's nose. In this manner, delivery of the nasal spray to the septum and the back of the nose, and the associated unwanted outcomes thereof, may be avoided. Following delivery of the nasal spray to the lateral wall of the first nasal cavity, the nozzle 204 of the nasal spray delivery device 200 may be removed from the first guide element 104 and may be similarly inserted into the second guide element 104. The nasal spray device 200 may be similarly activated to deliver the nasal spray to the lateral wall of the second nasal cavity via the second guide element 104. Following delivery of the nasal spray, the delivery guide 100 may be removed from the patient's nose.

Figure 3A:
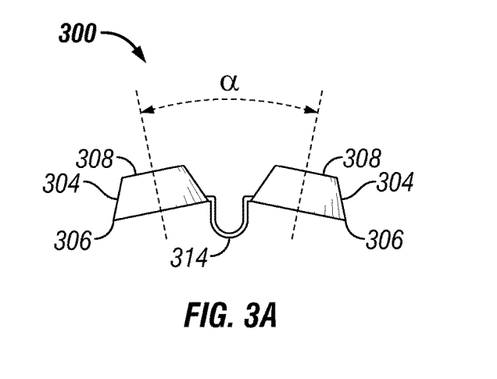
FIG. 3A shows a front view of a nasal spray delivery guide according to one example embodiment of the present disclosure, the nasal spray delivery guide in a stable conformation.
Figure 3B:
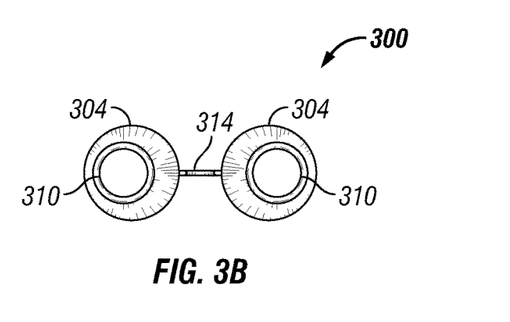
FIG. 3B shows a top view of the nasal spray delivery guide of FIG. 3A in the stable conformation.

FIGS. 3A and 3B show a nasal spray delivery guide 300 for facilitating delivery of a nasal spray into a patient's nose, according to another example embodiment of the present disclosure. The delivery guide 300 may include various elements corresponding to those described above with respect to the delivery guide 100, which elements may be formed, oriented, and configured to function in a manner similar to that described above. As is shown, the delivery guide 300 may include a pair of guide elements 304 configured to be inserted at least partially into respective nostrils of the patient and to receive at least a portion of a nasal spray delivery device 200 therein. Each guide element 304 may have a base end 306, a tip end 308, and an aperture 310 extending longitudinally therethrough from the base end 306 to the tip end 308. The delivery guide 300 also may include a flexible connector element 314 attached to and extending between the guide elements 304. Certain structural and functional differences between the delivery guide 300 and the delivery guide 100 are described as follows.

As is shown, the flexible connector element 314 may be in the form of a rod. In some embodiments, the rod may have a contoured shape when viewed from the front of the delivery guide 300, such as a "V" shape or a "U" shape (as is shown in FIGS. 3A and 3B). The rod may be solid or hollow, and may be formed of one material or a composite of materials. In various embodiments, an axial cross-section of the rod may have a generally constant circular, square, or rectangular shape, or may have a varying shape. In some embodiments, the axial cross-section of the rod may have a narrow rectangular cross section, as is shown, such that the rod is in the form of a thin strip.

The flexible connector element 314 may have at least one stable conformation in which an angle $\alpha$ between the longitudinal axes of the guide elements 304 is fixed, as is shown in FIGS. 3A and 3B. In some embodiments, the fixed angle $\alpha$ between the longitudinal axes of the guide elements 304 may be between approximately 10 degrees and approximately 30 degrees, or between approximately 15 degrees and approximately 25 degrees, or approximately 20 degrees. In this manner, upon insertion of the guide elements 304 into the patient's nostrils, each guide element 304 may be configured to direct a nasal spray to a lateral wall of the respective nostril, avoiding the septum and the back of the nose. Specifically, each guide element 304 may be configured to direct the nasal spray to the lateral wall at an angle from the septum that is equal to approximately one-half of the angle $\alpha$ between the longitudinal axes of the guide elements 304. Further, upon insertion of the guide elements 304 into the patient's nostrils, each guide element 304 may be configured to direct the nasal spray to the lateral wall at an angle from the floor of the patient's nose of between approximately 20 degrees and approximately 40 degrees, or between approximately 25 degrees and approximately 35 degrees, or approximately 30 degrees.

The rod may be flexible enough such that it may be temporarily deformed into a non-stable conformation under physical pressure typical of the human hand (for example, by application of a force of between approximately 0.5 Newtons and approximately 15 Newtons), although the rod will return to its stable conformation after such pressure is released. For example, the rod may be temporarily deformed into a non-stable, compressed conformation (with the ends of the rod pressed toward one another) in which the longitudinal axes of the guide elements 304 are parallel to one another (i.e., the angle $\alpha$ between the longitudinal axes of the guide elements 104 is zero). In some embodiments, the rod may have flattened surfaces along opposite sides of the rod (facing away from one another) such that the rod may be more easily grasped and squeezed into the non-stable, compressed conformation. In this manner, the rod may serve as a handle as well as a connecting element.

In some embodiments, the rod may be formed of a metal, such as a spring steel, stainless steel, or other metal of suitable stiffness and flexibility, a polymer, or other suitable material. In some embodiments, the rod may be formed of, or may be coated with, the same polymer as the guide elements 304.

In some embodiments in which the delivery guide 300 includes the flexible connector element 314 in the form of a rod, the delivery guide 300 may be manufactured by injection molding the rod and the guide elements 304 in the stable conformation in which an angle $\alpha$ between the longitudinal axes of the guide elements 304 is fixed. In some embodiments, the fixed angle $\alpha$ between the longitudinal axes of the guide elements 304 may be between approximately 10 degrees and approximately 30 degrees, or between approximately 15 degrees and approximately 25 degrees, or approximately 20 degrees.

In some embodiments, the rod may be formed with flanges on each end which may be affixed to outer surfaces of the guide elements 304, respectively, via glue, a weld, a rivet, or other affixing means. Alternatively, the flanges may be molded into the walls of the guide elements 304, respectively. In some embodiments, the rod may be formed with rings on each end which may be affixed to or incorporated into the guide elements 304, respectively, for example about the base ends 306 of the guide elements 304 or another location on the guide elements 304. In some embodiments in which the rod is formed with rings on each end, each of the rings may include a flange extending thereabout to facilitate grasping the delivery guide 300 and applying pressure thereto in order to move the delivery guide 300 from the stable conformation into the non-stable, compressed conformation.

Figure 4A:
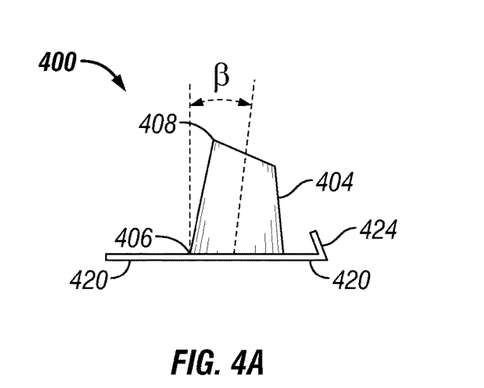
FIG. 4A shows a front view of a nasal spray delivery guide according to one example embodiment of the present disclosure, the nasal spray delivery guide in a stable conformation.
Figure 4B:
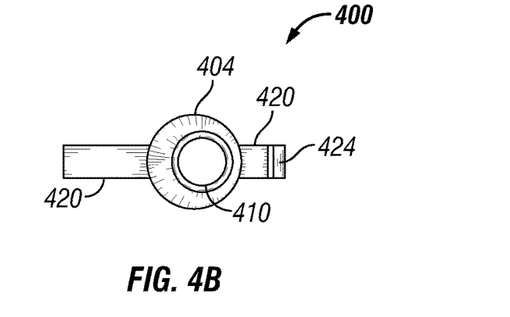
FIG. 4B shows a top view of the nasal spray delivery guide of FIG. 4A in the stable conformation.
Figure 5A:
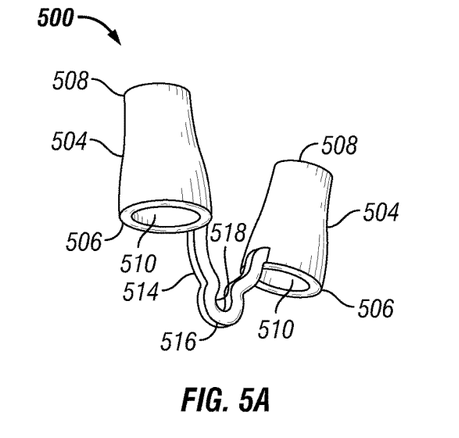
FIG. 5A shows a bottom perspective view of a nasal spray delivery guide according to one example embodiment of the present disclosure, the nasal spray delivery guide in a stable conformation.
Figure 5B:
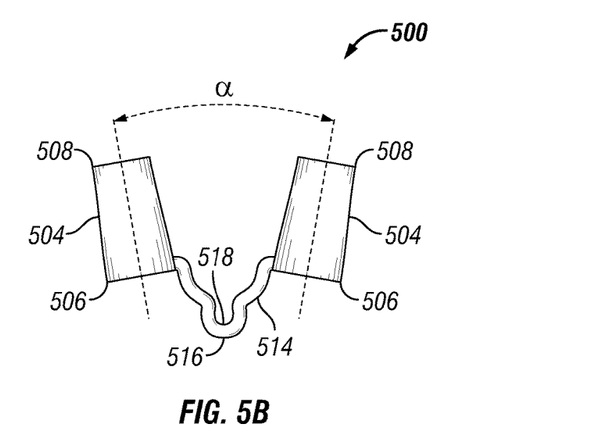
FIG. 5B shows a front view of the nasal spray delivery guide of FIG. 5A in the stable conformation.
Figure 5C:
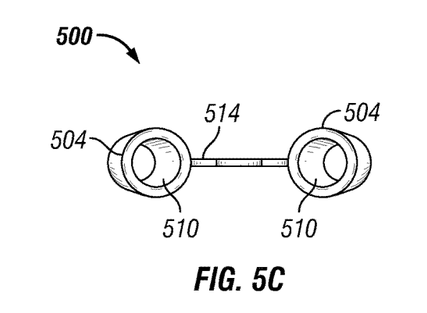
FIG. 5C shows a bottom view of the nasal spray delivery guide of FIG. 5A in the stable conformation.
Figure 5D:
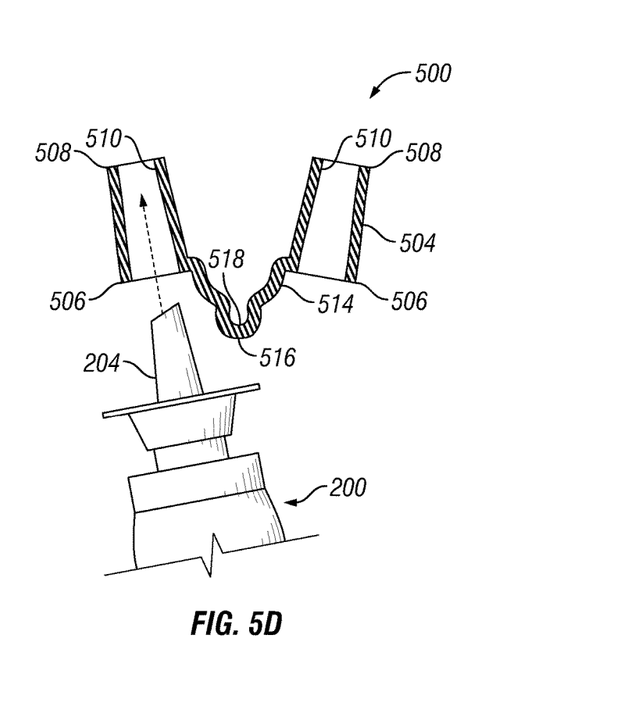
FIG. 5D shows a front cross-sectional view of the nasal spray delivery guide of FIG. 5A in the stable conformation and a nasal spray delivery device approaching a guide element of the nasal spray delivery guide.

FIGS. 4A and 4B show a nasal spray delivery guide 400 for facilitating delivery of a nasal spray into a patient's nose, according to another example embodiment of the present disclosure. The delivery guide 400 may include various elements corresponding to those described above with respect to the delivery guide 100, which elements may be formed, oriented, and configured to function in a manner similar to that described above. As is shown, the delivery guide 400 may include a single guide element 404 configured to be inserted at least partially into a nostril of the patient and to receive at least a portion of a nasal spray delivery device 200 therein. The guide element 404 may have a base end 406, a tip end 408, and an aperture 410 extending longitudinally therethrough from the base end 406 to the tip end 408. Certain structural and functional differences between the delivery guide 400 and the delivery guide 100 are described as follows.

The delivery guide 400 also may include at least one wing 420 extending away from the guide element 404. Specifically, the delivery guide 400 may include a pair of wings 420 extending away from the guide element 404 in substantially opposite directions, as is shown. In some embodiments, one or both of the wings 420 may include a clamping tab 424 extending upward and inward towards the guide element 404. In this manner, upon insertion of the guide element 404 into the patient's nostril, the clamping tab 424 may engage an outer surface of the nose such that the delivery guide 400 is secured in place for use.

In some embodiments, the wings 420 may be formed of a metal, such as a spring steel, stainless steel, or other metal of suitable stiffness and flexibility, a polymer, or other suitable material. In some embodiments, the wings 420 may be formed of, or may be coated with, the same polymer as the guide elements 404.

In some embodiments, the delivery guide 400 may be manufactured by injection molding the wings 420 and the guide elements 404 in a stable conformation in which an angle $\beta$ between the longitudinal axis of the guide element 404 and an axis perpendicular to the wings 420 is fixed. In some embodiments, the fixed angle $\beta$ between the longitudinal axis of the guide element 404 and an axis perpendicular to the wings 420 may be between approximately 5 degrees and approximately 15 degrees, or between approximately 7.5 degrees and approximately 12.5 degrees, or approximately 10 degrees. In this manner, upon insertion of the guide element 404 into the patient's nostril, the guide element 404 may be configured to direct a nasal spray to a lateral wall of the nostril, avoiding the septum and the back of the nose. Specifically, the guide element 404 may be configured to direct the nasal spray to the lateral wall at an angle from the septum that is approximately equal to the angle β between the longitudinal axis of the guide element 404 and an axis perpendicular to the wings 420. Further, upon insertion of the guide element 404 into the patient's nostril, the guide element 104 may be configured to direct the nasal spray to the lateral wall at an angle from the floor of the patient's nose of between approximately 20 degrees and approximately 40 degrees, or between approximately 25 degrees and approximately 35 degrees, or approximately 30 degrees.

FIGS. 5A-5D show a nasal spray delivery guide 500 for facilitating delivery of a nasal spray into a patient's nose, according to another example embodiment of the present disclosure. The delivery guide 500 may include various elements corresponding to those described above with respect to the delivery guide 100, which elements may be formed, oriented, and configured to function in a manner similar to that described above. As is shown, the delivery guide 500 may include a pair of guide elements 504 configured to be inserted at least partially into respective nostrils of the patient and to receive at least a portion of a nasal spray delivery device 200 therein. Each guide element 504 may have a base end 506, a tip end 508, and an aperture 510 extending longitudinally therethrough from the base end 506 to the tip end 508. The delivery guide 500 also may include a flexible connector element 514 attached to and extending between the guide elements 504. Certain structural and functional differences between the delivery guide 500 and the delivery guide 100 are described as follows.

As is shown, the flexible connector element 514 may be in the form of a rod. In some embodiments, the rod may have a contoured shape when viewed from the front of the delivery guide 500, such as a "V" shape or a "U" shape (as is shown in FIGS. 5A-5D). The rod may be solid or hollow, and may be formed of one material or a composite of materials. In various embodiments, an axial cross-section of the rod may have a generally constant circular, square, or rectangular shape, or may have a varying shape. In some embodiments, the axial cross-section of the rod may have a narrow rectangular shape, as is shown, such that the rod is in the form of a thin strip. In some embodiments, the flexible connector element 514 may include a small semi-circular bend 516 positioned at or near an apex thereof and defining a small notch 518 therein, as is shown in FIGS. 5A-5D. The function of the bend 516 and the notch 518 is described herein below.

The flexible connector element 514 may have at least one stable conformation in which an angle α between the longitudinal axes of the guide elements 504 is fixed, as is shown in FIGS. 5A-5D. In some embodiments, the fixed angle α between the longitudinal axes of the guide elements 504 may be between approximately 10 degrees and approximately 30 degrees, or between approximately 15 degrees and approximately 25 degrees, or approximately 20 degrees. In this manner, upon insertion of the guide elements 504 into the patient's nostrils, each guide element 504 may be configured to direct a nasal spray to a lateral wall of the respective nostril, avoiding the septum and the back of the nose. Specifically, each guide element 504 may be configured to direct the nasal spray to the lateral wall at an angle from the septum that is equal to approximately one-half of the angle α between the longitudinal axes of the guide elements 504. Further, upon insertion of the guide elements 504 into the patient's nostrils, each guide element 504 may be configured to direct the nasal spray to the lateral wall at an angle from the floor of the patient's nose of between approximately 20 degrees and approximately 40 degrees, or between approximately 25 degrees and approximately 35 degrees, or approximately 30 degrees.

The rod may be flexible enough such that it may be temporarily deformed into a non-stable conformation under physical pressure typical of the human hand (for example, by application of a force of between approximately 0.5 Newtons and approximately 15 Newtons), although the rod will return to its stable conformation after such pressure is released. For example, the rod may be temporarily deformed into a non-stable, compressed conformation (with the ends of the rod pressed toward one another) in which the longitudinal axes of the guide elements 504 are parallel to one another (i.e., the angle α between the longitudinal axes of the guide elements 104 is zero). In some embodiments, the rod may have flattened surfaces along opposite sides of the rod (facing away from one another) such that the rod may be more easily grasped and squeezed into the non-stable, compressed conformation. In this manner, the rod may serve as a handle as well as a connecting element.

In some embodiments, the rod may be formed of a metal, such as a spring steel, stainless steel, or other metal of suitable stiffness and flexibility, a polymer, or other suitable material. In some embodiments, the rod may be formed of, or may be coated with, the same polymer as the guide elements 504.

In some embodiments in which the delivery guide 500 includes the flexible connector element 514 in the form of a rod, the delivery guide 500 may be manufactured by injection molding the rod and the guide elements 504 in the stable conformation in which an angle α between the longitudinal axes of the guide elements 504 is fixed. In some embodiments, the fixed angle α between the longitudinal axes of the guide elements 504 may be between approximately 10 degrees and approximately 30 degrees, or between approximately 15 degrees and approximately 25 degrees, or approximately 20 degrees.

In some embodiments, the rod may be formed with flanges on each end which may be affixed to outer surfaces of the guide elements 504, respectively, via glue, a weld, a rivet, or other affixing means. Alternatively, the flanges may be molded into the walls of the guide elements 504, respectively. In some embodiments, the rod may be formed with rings on each end which may be affixed to or incorporated into the guide elements 504, respectively, for example about the base ends 506 of the guide elements 504 or another location on the guide elements 504. In some embodiments in which the rod is formed with rings on each end, each of the rings may include a flange extending thereabout to facilitate grasping the delivery guide 500 and applying pressure thereto in order to move the delivery guide 500 from the stable conformation into the non-stable, compressed conformation.

In another aspect, the present disclosure provides a nasal spray delivery system including a nasal spray delivery device, a nasal spray delivery guide, and a clip for removably coupling the nasal spray delivery guide to the nasal spray delivery device when the system is not in use. In this manner, the clip prevents the nasal spray delivery guide from being misplaced or damaged when not in use.

Figure 6:
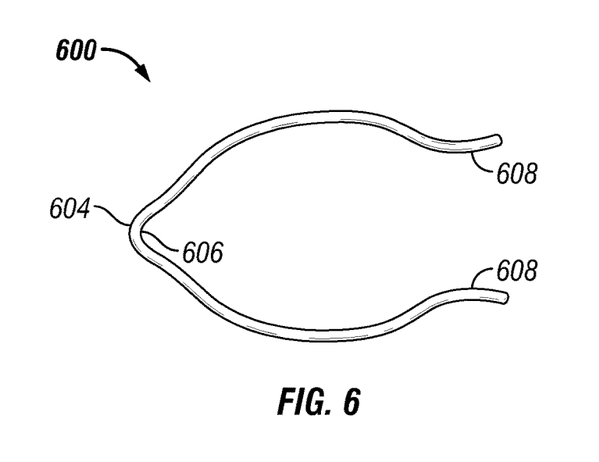
FIG. 6 shows a top view of a clip according to one example embodiment of the present disclosure, the clip in a stable conformation.
Figure 7A:
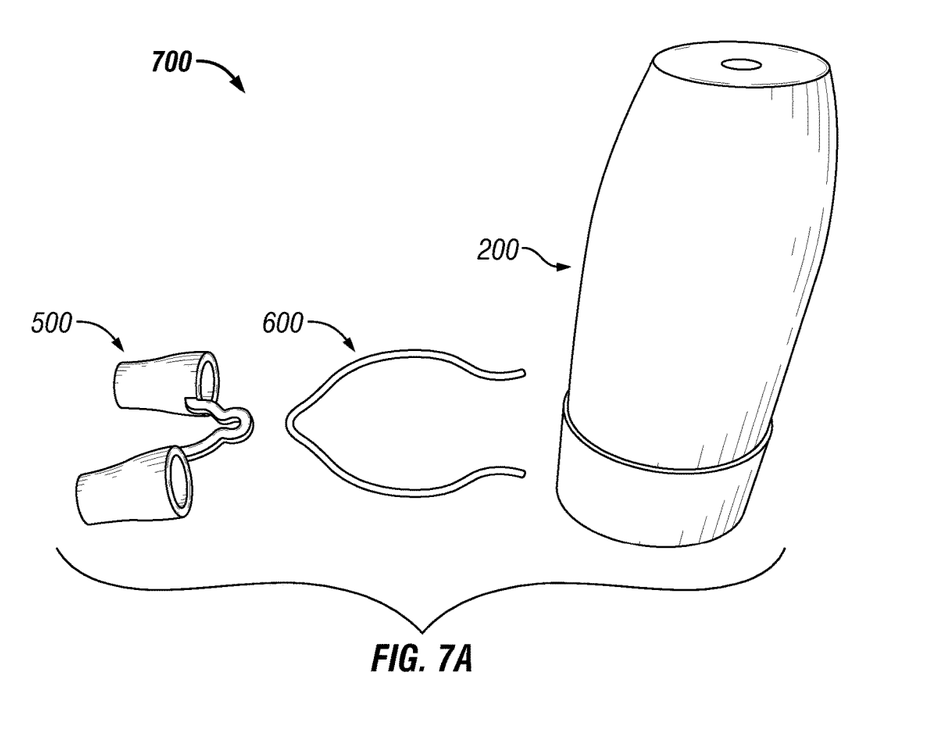
FIG. 7A shows a top perspective view of a nasal spray delivery system according to one example embodiment of the present disclosure, the nasal spray delivery system in a disassembled state.
Figure 7B:
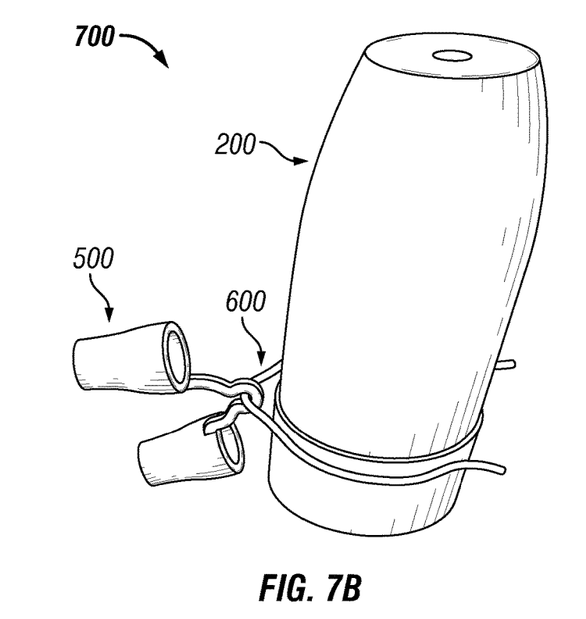
FIG. 7B shows a top perspective view of the nasal spray delivery system of FIG. 7A in an assembled state.
Figure 7C:
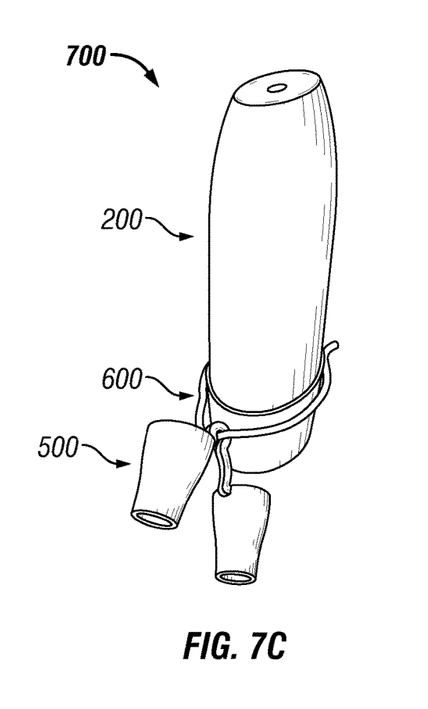
FIG. 7C shows a top perspective view of the nasal spray delivery system of FIG. 7A in the assembled state.
Figure 7D:
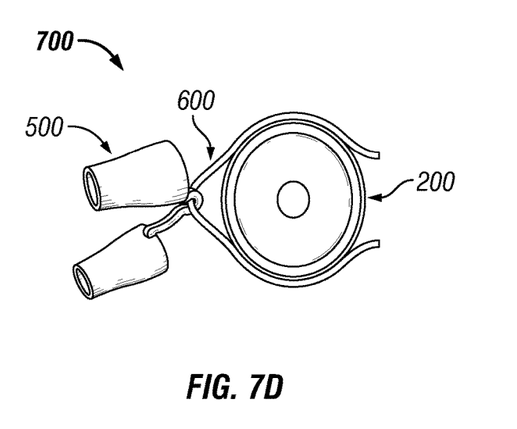
FIG. 7D shows a top view of the nasal spray delivery system of FIG. 7A in the assembled state.

FIG. 6 shows show a clip 600 for removably coupling a nasal spray delivery guide to a nasal spray delivery device, according to one embodiment of the present disclosure. In some embodiments, the clip 600 may be formed as a contoured wire generally having a "C" shape, as is shown. In some embodiments, the cross-section of the wire may have a narrow rectangular shape, as is shown, such that the wire is in the form of a thin strip and may be easily grasped by a user. In other embodiments, the cross-section of the wire may have a circular shape. The clip 600 may include a small semi-circular bend 604 positioned at or near an apex thereof and defining a small notch 606 therein. In some embodiments, the ends 608 of the clip 600 may be bent outwards, as is shown.

In various embodiments, the clip 600 may be formed of a metal, such as a spring steel, stainless steel, or other metal of suitable stiffness and flexibility, a polymer, or other suitable material. In some embodiments, the clip 600 may be coated with a suitable material, such as a polymer.

Figure 8:
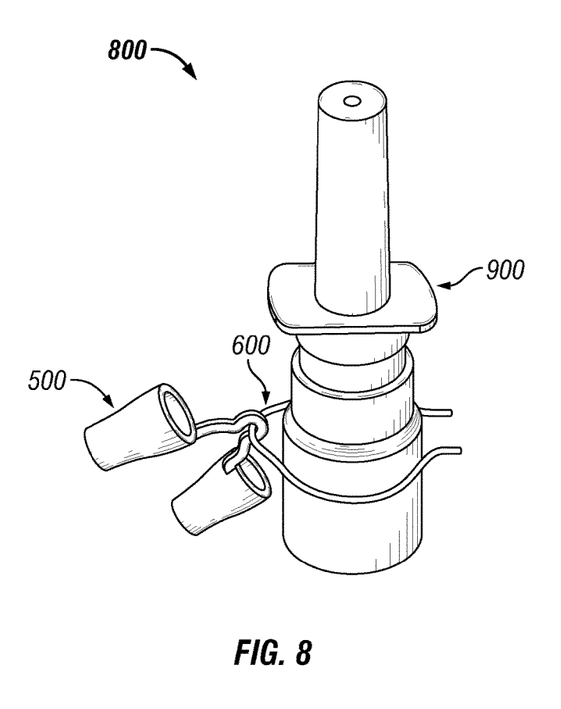
FIG. 8 shows a top perspective view of a nasal spray delivery system according to one example embodiment of the present disclosure, the nasal spray delivery system in an assembled state.

FIGS. 7A-7D show a nasal spray delivery system 700 according to one embodiment of the present disclosure. The delivery system 700 may include the nasal spray delivery device 200, the nasal spray delivery guide 500, and the clip 600. The delivery device 200 may be any type of nasal spray bottle or similar device having a generally circular, oval, or oblong cross section. In use, the clip 600 may be removably attached to a portion of the delivery device 200 by pushing the open portion of the clip 600 over the desired portion of the delivery device 200. The bent shape of the ends 608 of the clip 600 may ease spreading of the clip 600 as it is pushed over the delivery device 200. Due its flexible and resilient nature, the clip 600 may remain attached to the delivery device 200 until the clip 600 is pulled therefrom in an opposite direction. As is shown, the semi-circular bend 604 of the clip 600 may engage the semi-circular bend 516 of the flexible connector element 514 of the delivery guide 500 such that the delivery guide 500 is removably coupled to the delivery device 200. In some embodiments, the notch 606 of the clip 600 may be larger than the cross-section of the flexible connector element 514 such that the flexible connector element 514 is not pressed against the delivery device 200 when coupled thereto. In this manner, the integrity of the delivery guide 500, specifically the flexible connector element 514, may be maintained during storage. In use, the clip 600 may be removably attached to a variety of nasal spray delivery devices having different cross-sectional shapes and different dimensions. For example, FIG. 8 shows another embodiment of a nasal spray delivery system 800 including a nasal spray delivery device 900 having a different cross-sectional shape and different dimensions. Due to its flexible and resilient nature, the clip 600 may accommodate such differences with ease.

Many modifications and other embodiments of the devices, systems, and methods provided in the present disclosure will come to mind to one skilled in the art upon having the benefit of the teachings presented herein through the foregoing descriptions and the associated drawings. Therefore, it is to be understood that the present invention is not to be limited to the specific example embodiments disclosed and that modifications and other embodiments are intended to be included within the scope of the appended claims. Although specific terms are employed herein, they are used in a generic and descriptive sense only and not for purposes of limitation.

The invention claimed is:

1. A nasal spray delivery guide comprising:
  a pair of guide elements spaced apart from one another and configured to be at least partially inserted into respective nostrils of a patient, each guide element comprising an aperture extending therethrough from a base end to a tip end of the guide element;
  a flexible connector element attached to and extending between the guide elements;
  a wing extending away from one of the guide elements; and
  a clamping tab extending away from the wing and upwards and towards one of the guide elements;
  wherein the delivery guide has a stable conformation in which an angle between longitudinal axes of the guide elements is between approximately 10 degrees and approximately 30 degrees, and in which an angle between the longitudinal axis of one of the guide elements and an axis perpendicular to the wing is between approximately 5 degrees and approximately 15 degrees.

2. The nasal spray delivery guide of claim 1, wherein each guide element is configured to direct a nasal spray to a lateral wall of a respective nasal cavity at an angle of between approximately 20 degrees and approximately 40 degrees from a floor of the patient's nose.

3. The nasal spray delivery guide of claim 1, wherein the guide elements have a generally conical shape with axial cross sections decreasing from the base end to the tip end.

4. The nasal spray delivery guide of claim 1, wherein the angle between longitudinal axes of the guide elements is between approximately 15 degrees and approximately 25 degrees when the delivery device is in the stable conformation.

5. The nasal spray delivery guide of claim 1, wherein the delivery guide is configured to be temporarily deformed into a non-stable conformation in which the longitudinal axes of the guide elements are substantially parallel to one another.

6. The nasal spray delivery device of claim 5, wherein the delivery guide is configured to be temporarily deformed into the non-stable conformation upon application of a force of between approximately 0.5 Newtons and approximately 15 Newtons.

7. The nasal spray delivery device of claim 6, wherein the delivery guide is configured to return to the stable conformation upon removal of the force.

8. The nasal spray delivery device of claim 1, wherein the flexible connector element is formed as a rod attached to and extending between the guide elements.

9. The nasal spray delivery device of claim 8, wherein the rod is configured to be temporarily deformed into a non-stable conformation in which the longitudinal axes of the guide elements are generally parallel to one another.

10. The nasal spray delivery device of claim 1, wherein the flexible connector element is formed as a sheet attached to and extending between the guide elements.

11. The nasal spray delivery device of claim 10 wherein the sheet is configured to be temporarily deformed into a non-stable conformation in which the longitudinal axes of the guide elements are generally parallel to one another.

12. A method for delivering a nasal spray into a patient's nose, the method comprising:
  providing a nasal spray delivery guide comprising:
    a pair of guide elements spaced apart from one another, each guide element comprising an aperture extending therethrough from a base end to a tip end of the guide element;
    a flexible connector element attached to and extending between the guide elements;
    a wing extending away from one of the guide elements; and a clamping tab extending away from the wing and upwards and towards one of the guide elements;

wherein the delivery guide has a stable conformation in which an angle between longitudinal axes of the guide elements is between approximately 10 degrees and approximately 30 degrees, and in which an angle between the longitudinal axis of one of the guide elements and an axis perpendicular to the wing is between approximately 5 degrees and approximately 15 degrees;

inserting the guide elements at least partially into respective nostrils of the patient;

inserting at least a portion of a nasal spray delivery device into one of the guide elements; and activating the nasal spray delivery device to deliver a nasal spray to a lateral wall of a respective nasal cavity.

13. The method of claim 12, wherein each guide element is configured to direct the nasal spray to the lateral wall of the respective nasal cavity at an angle of between approximately 20 degrees and approximately 40 degrees from a floor of the patient's nose, and wherein inserting at least the portion of the nasal spray delivery device into one of the guide elements comprises inserting a nozzle of the nasal spray delivery device into the aperture of the one of the guide elements such that the nasal spray delivery device is oriented to deliver the nasal spray to the lateral wall of the respective nasal cavity.

14. The method of claim 12, wherein the delivery guide is configured to be temporarily deformed into a non-stable conformation in which the longitudinal axes of the guide elements are generally parallel to one another.

15. The method of claim 14, further comprising, prior to inserting the guide elements at least partially into respective nostrils of the patient, temporarily deforming the delivery guide into the non-stable conformation.

16. The method of claim 15, wherein temporarily deforming the delivery guide into the non-stable conformation comprises applying a force of between approximately 0.5 Newtons and approximately 15 Newtons to the delivery guide.

17. The method of claim 15, further comprising, after inserting the guide elements at least partially into respective nostrils of the patient, allowing the delivery guide to return to the stable conformation.

18. A nasal spray delivery system comprising:
a nasal spray delivery device;
a nasal spray delivery guide comprising:
a pair of guide elements spaced apart from one another and configured to be at least partially inserted into respective nostrils of a patient, each guide element comprising an aperture extending therethrough from a base end to a tip end of the guide element;
a flexible connector element attached to and extending between the guide elements;
a wing extending away from one of the guide elements; and
a clamping tab extending away from the wing and upwards and towards one of the guide elements;
wherein the delivery guide has a stable conformation in which an angle between longitudinal axes of the guide elements is between approximately 10 degrees and approximately 30 degrees, and in which an angle between the longitudinal axis of one of the guide elements and an axis perpendicular to the wing is between approximately 5 degrees and approximately 15 degrees; and
a clip removably attached to the nasal spray delivery device;
wherein the nasal spray delivery guide is removably coupled to the nasal spray delivery device via the clip.

19. The nasal spray delivery system of claim 18, wherein the clip is formed as a contoured wire having a generally "C" shape.

20. The nasal spray delivery system of claim 19, wherein the clip comprises a semi-circular bend positioned at or near an apex thereof and defining a notch therein, and wherein the semi-circular bend of the clip engages the flexible connector element of the delivery guide.

21. The nasal spray delivery system of claim 18, wherein the flexible connector element comprising a semi-circular bend defining a notch, and wherein the nasal spray delivery guide is removably coupled by the notch of the bend to the nasal spray delivery device via the clip.

* * * * *